US009539028B2

(12) United States Patent
Dall et al.

(10) Patent No.: US 9,539,028 B2
(45) Date of Patent: Jan. 10, 2017

(54) BONE FIXATION DEVICE

(71) Applicant: EVOLVE ORTHOPEDICS SA, Montreux (CH)

(72) Inventors: Vagn Erik Dall, Slough (GB); Morten Beyer, Roedkaersbro (DK)

(73) Assignee: EVOLVE ORTHOPEDICS SA, Montreux (CH)

( * ) Notice: Subject to any disclaimer, the term of this patent is extended or adjusted under 35 U.S.C. 154(b) by 358 days.

(21) Appl. No.: 14/367,274

(22) PCT Filed: Dec. 20, 2012

(86) PCT No.: PCT/EP2012/076486
§ 371 (c)(1),
(2) Date: Jun. 20, 2014

(87) PCT Pub. No.: WO2013/092913
PCT Pub. Date: Jun. 27, 2013

(65) Prior Publication Data
US 2014/0371801 A1    Dec. 18, 2014

(30) Foreign Application Priority Data

Dec. 20, 2011 (GB) .................................. 1122013.4

(51) Int. Cl.
*A61B 17/64*    (2006.01)
*A61B 17/60*    (2006.01)
(Continued)

(52) U.S. Cl.
CPC ........... *A61B 17/6416* (2013.01); *A61B 17/58* (2013.01); *A61B 17/60* (2013.01); *A61B 17/6441* (2013.01);
(Continued)

(58) Field of Classification Search
CPC ..... A61B 17/60; A61B 17/64; A61B 17/6416; A61B 17/6441; A61B 17/6458; A61B 17/6466; A61B 17/68; A61B 17/70; A61B 17/7001; A61B 17/7049; A61B 17/705
See application file for complete search history.

(56) References Cited

U.S. PATENT DOCUMENTS 5,393,161 A * 2/1995 Mata .................. A61B 17/6416
403/112
5,746,741 A    5/1998 Kraus et al.
(Continued)

FOREIGN PATENT DOCUMENTS

| CN | 1051855 A | 6/1991 |
|---|---|---|
| CN | 101856263 A | 10/2010 |
| EP | 1309281 B1 | 3/2008 |
| FR | 2831792 A1 | 5/2003 |
| GB | 2375051 A | 11/2002 |

OTHER PUBLICATIONS

Patent Cooperation Treaty, Notification of Transmittal of the International Search Report and the Written Opinion of the International Searching Authority for Application No. PCT/EP2012/076486 dated Apr. 17, 2013, 8 pages.
(Continued)

*Primary Examiner* — Larry E Waggle, Jr.
(74) *Attorney, Agent, or Firm* — Hoffman Warnick LLC

(57) ABSTRACT

A bone fixation device comprises a plurality of brackets (6, 8, 42-48), each defining a surface formed with at least one recess (56, 58). Part of a ball (12-18, 52, 54) is mounted in each recess with an exposed face formed with a groove (24, 26, 52, 54) for receiving a fixation rod or bone screw. The brackets are capable of being brought together such that at least one pair of exposed ball faces are in juxtaposition with the grooves defining a sleeve for a fixation rod or bone screw, and means (10, 50) are included for urging the brackets and the exposed ball faces towards each other to clamp a fixation rod or bone screw between a pair of juxtaposed ball faces. Normally, the recesses and ball parts are arranged such that as the brackets are brought together at least two pairs of ball parts are in juxtaposition, forming two sleeves for fixation rods or bone screws.

20 Claims, 3 Drawing Sheets

(51) Int. Cl.
*A61B 17/68* (2006.01)
*A61B 17/70* (2006.01)
*A61B 17/58* (2006.01)

(52) U.S. Cl.
CPC ....... *A61B 17/6458* (2013.01); *A61B 17/6466* (2013.01); *A61B 17/68* (2013.01); *A61B 17/7001* (2013.01); *A61B 17/705* (2013.01); *A61B 17/7049* (2013.01)

(56) References Cited

U.S. PATENT DOCUMENTS

| | | |
|---|---|---|
| 7,048,735 B2 | 5/2006 | Ferrante et al. |
| 7,507,240 B2 * | 3/2009 | Olsen ................ A61B 17/6416 606/57 |
| 2007/0231059 A1 | 10/2007 | Mullaney |
| 2009/0131985 A1 | 5/2009 | Mazda et al. |
| 2013/0066386 A1 | 3/2013 | Biedermann et al. |

OTHER PUBLICATIONS

State Intellectual Property Office of the People's Republic of China, The First Office Action for Application No. 201280062946X dated Dec. 16, 2015, 18 pages.
Evolve Orthopedics SA; Second Office Action for CN Application No. 201280062946X; Issued Aug. 10, 2016; 16 Pages.

* cited by examiner

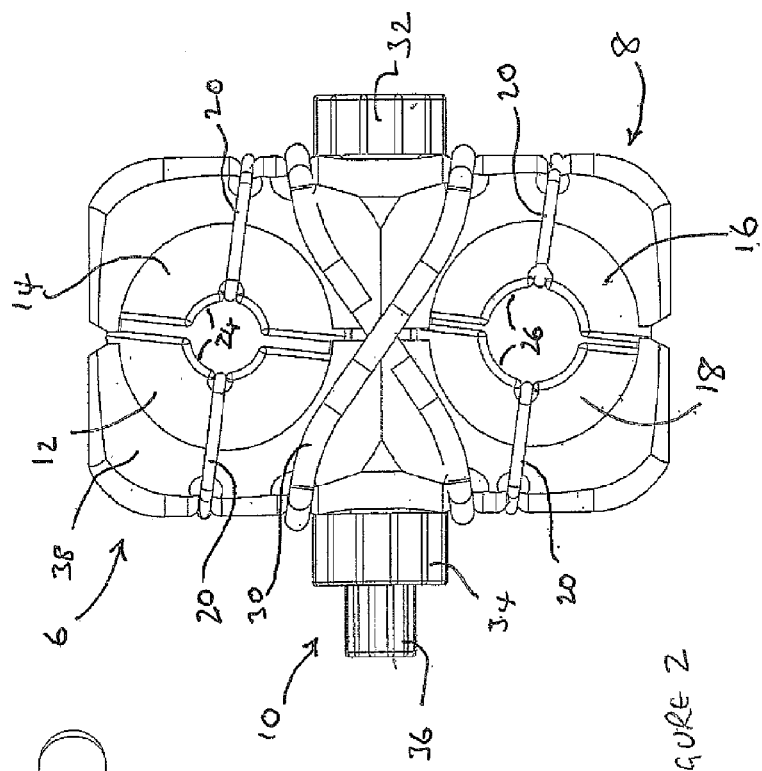
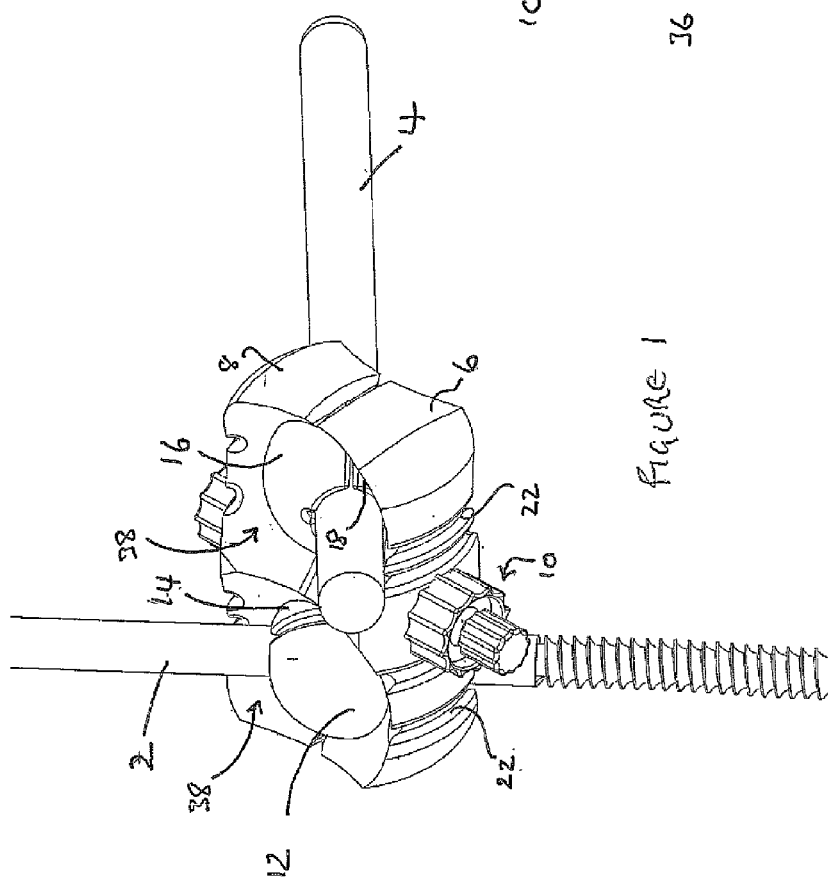

BONE FIXATION DEVICE

This invention relates to gripping devices, and has particular use in surgical applications. It is especially useful in applications where bones or bone elements require external fixation. Such devices are commonly known as bone fixation devices, and are used to couple fixation rods to each other and to cortical bone screws secured in a bone or bone part requiring fixation. Such devices are described in British Patent Specification No. 2,375,051A European Patent No: 1,309,281, both incorporated by reference. Another external fixation system for surgical use is disclosed in U.S. Pat. No. 7,048,735, also incorporated by reference.

In orthopedic surgery where bone fixation is required, devices for securing fixation rods must be fitted and manipulated in awkward locations and with great care. The aim of the present invention is to provide a device which can be easily installed, adjusted and secured, with an installed rod having the widest possible range of orientations relative to another rod or bone screw fitted to the device. According to the invention, a bone fixation device comprises a plurality of brackets, each defining a surface formed with at least one recess. Part of a ball is mounted in each recess with an exposed face formed with a groove for receiving a fixation rod or bone screw. The brackets are capable of being brought together such that at least one pair of exposed ball faces are in juxtaposition with the grooves defining a sleeve for a fixation rod or bone screw, and means are included for urging the brackets and the exposed ball faces towards each other to clamp a fixation rod or bone screw between a pair of juxtaposed ball faces. Normally, the recesses and ball parts are arranged such that as the brackets are brought together at least two pairs of ball parts are in juxtaposition, forming two sleeves for fixation rods or bone screws. Typically, a device according to the invention has an even number of brackets arranged in at least one pair, with each bracket defining a surface with a single recess for a ball part mounted therein. In this embodiment multiple pairs of brackets can be stacked, and arranged to hold multiple rods or screws. In one preferred embodiment, two pairs will be stacked with a single common mechanism for urging the brackets together with the rods or screws or rod and screw in place in the respective sleeves.

In another embodiment, the device of the invention has two brackets, each bracket defining a surface formed of at least two recesses for ball parts mounted therein. In this arrangement, as in the embodiment described above, a single mechanism can be provided to urge the brackets together to hold two rods, two screws or a rod and a screw relative to one another.

In another arrangement, not all the brackets in a device of the invention define surfaces formed with the same number of recesses. In this embodiment, the brackets are arranged with one defining a surface formed with a plurality of recesses whereby exposed faces of ball parts therein can be in juxtaposition with the exposed faces of ball parts mounted in the surfaces of at least two other brackets.

The recesses in the bracket surfaces for the ball parts can conveniently be provided in the form of arcuate channels. On either side of each channel the respective bracket can be shaped to form lateral recesses having the shape of shallow frusto-cones. This ensures that a rod or screw received in the respective part balls can be directed in the widest possible range of orientations.

A device according to the invention is in modular form, and ultimately held assembled by the means urging the brackets and exposed ball faces towards each other. Prior thereto, the part-balls can be held in their respective recesses by resilient ties, typically in the form of elastic O-rings. The brackets themselves can also be held together by resilient ties, again in the form of elastic O-rings. This allows the brackets to be separated with the part-balls attached, to allow for insertion of a fixation rod or bone screw in one of the defined sleeves, or for mounting the device on a rod or bone screw if the latter is already in place. The brackets and/or the part-balls can be formed with a chamfered surface to facilitate this installation. It will be appreciated that the brackets can be pivoted relative to one another to allow separate installation in one or other of the grooves.

Normally, a device according to the invention will be adapted to couple two elements, but it will be appreciated that if a circumstance requires the device may be adapted to define three or more sleeves. This might be required for example, if two rods are required to be mounted on the same bone screw although generally, separate fixation devices would be used. It will be appreciated that different arrangements of brackets can be combined to create different frameworks of rods and/or screws.

The part-balls used in devices according to the invention will normally be solid, and each have outlines defining substantially a hemisphere. However, it is not essential that they are identical, so long as they provide for easy receipt of a fixation rod or bone screw when the brackets are separated. Typically then, the part of each part-ball face on the side of the groove past which a fixation rod or a bone screw will be installed, will be aligned with or close to the bracket edge. It is though, preferred that this part of the part-ball face is not aligned exactly with the bracket edge. In particular embodiments of the invention the space between these part-ball faces is closed by a section of the respective recess, adjacent the space between the brackets. This reduces the likelihood of a fixation rod being unintentionally withdrawn from the device during its assembly. Typically, these part-ball faces are substantially planar, and are in planes other than perpendicular to the axis along which the brackets are urged together during installation. It is preferred that a plane defining the juxtaposition of each pair of ball faces traverses the planes of the bracket surfaces when a fixation rod or bone screw is clamped between the ball faces. It will though, be appreciated that when a fixation rod or bone screw is installed in the device, neither the juxtaposed bracket faces nor the juxtaposed ball faces will normally be in contact with each other.

As noted above, in its modular form the ball parts can be held temporarily in their respective recesses in the brackets, and the brackets themselves can also be held together relatively loosely until the installed device is secured. Once the device is secured, these temporary ties can be superfluous, and may be biodegradable. If this feature is adopted, particular care must be taken when the devices are eventually removed and for this reason, there can be merit in at least the ties holding the balls in place remaining.

When a device according to the invention is installed, the brackets can be urged together by means of a locking screw. This can be a single screw extending through an opening in one of the brackets for engagement in a threaded section in the other bracket or brackets, or for extending through openings in the brackets for engagement with a threaded locknut on the other side. In other variations the locking screw can comprise male and female threaded parts extending respectively in aligned openings in the brackets for engagement within the assembled device. Whatever mechanism is employed, it is important to ensure that any locking screw is tightened to the right degree. According to one feature of the invention, this is accomplished by including on the locking device a torque limiting element specifically for tightening. The element is adapted to break off when the torque applied exceeds a pre-set limit. In order to minimise the risk of such an element being dropped, tightening should be completed using a wrench or other unit to which the element is or becomes attached.

Devices of the invention and their components can be made of any material suitable for the environments in which the devices are to be used. For surgical applications the selection of the materials is of course important, with stainless steel often being preferred. However, we have found that plastics materials and carbon fibre materials in particular, are suitable for devices of the invention. Moulded carbon nanotubes materials are particularly preferred. Another material is fibre reinforced polyphenylenesuiphide (PPS), which can be used at least for the part-ball elements.

The invention will now be described by way of example and with reference to the accompanying drawings wherein:

FIG. 1 is a perspective view of a device according to a first embodiment of the invention mounted on a bone screw, and supporting a fixation rod;

FIG. 2 is a side view of the device shown in FIG. 1 assembled prior to installation;

Figure 3:
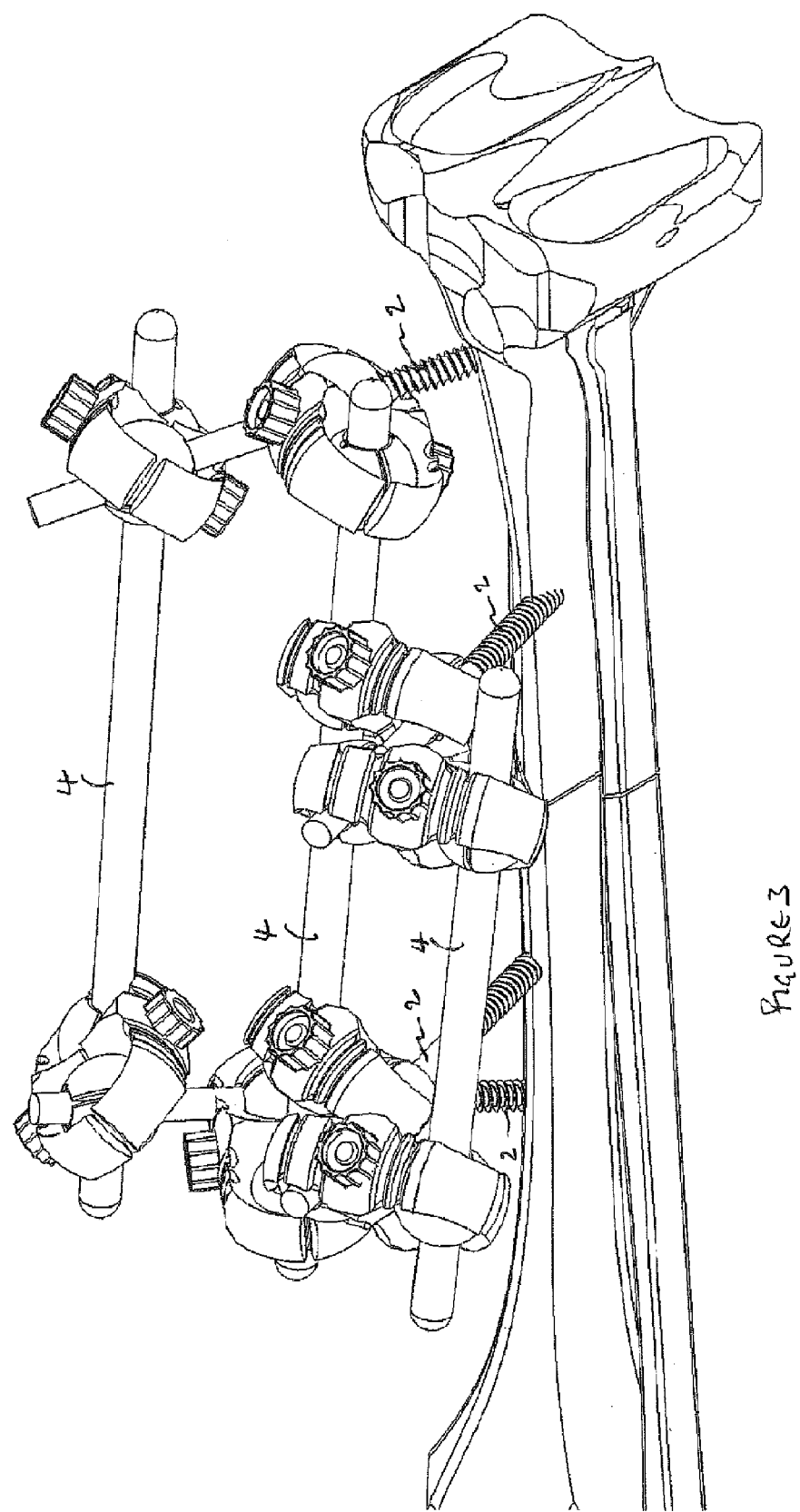
FIG. 3 illustrates how devices according to the invention can be used in a surgical application to fixate a bone fracture.

FIG. 1 shows a device according to the invention mounted on a bone screw 2, and supporting a fixation rod 4. The fixation device itself comprises two brackets 6,8 held together by a locking screw 10. The bone screw 2 is clamped between two ball parts 12,14 which are themselves held between juxtaposed recesses formed in the brackets 6 and 8. The fixation rod 4 is held in the same way between ball parts 16 and 18 received in similar recesses.

FIG. 1 shows a device of invention installed and secured. FIG. 2 shows the device in the form in which it would normally be supplied, with the locking screw installed but not tightened, with the other elements of the device held in place by resilient ties. The part-balls 12 and 14, and 16 and 18, are respectively held in place by elastic O-rings 20 which fit into channels 22 formed on the outer surfaces of the brackets 6 and 8. Grooves 24 and 26 are formed in the part-balls 12,14,16,18 to define sleeves for receiving fixation rods or bone screws, and at the base of each groove is formed a channel for receiving the respective O-ring 20.

In the form in which the device is supplied, the brackets 6 and 8 are themselves held together by two elastic O-rings 30. With these in place, the locking screw 10 can be removed, without disrupting the assembly. The brackets can be pivoted relative to each other against the resilient force of the O-rings 30, to admit a bone screw for example into the channel formed by grooves 26, and then in the opposite sense to admit a fixation rod into the channel formed by grooves 24. The device can then be maneuvered into the desired position on an installed bone screw with the fixation rod in the desired orientation, and the locking screw can then be installed.

As can be seen from FIG. 2, the part-balls 12,14 and 16,18 have a substantially hemispherical outline, with bases defining a plane of juxtaposition. The brackets 6 and 8 also define a plane of juxtaposition between surfaces in which recesses are formed to receive the part-balls, but as can be seen the planes of juxtaposition of the part-balls are inclined to that of the brackets, the former traversing the latter. This inclination is small; typically in the range 5° to 10° and preferably 7°, and does not interfere with the installation of a fixation rod or bone screw, as described above. It does though, reduce the risk of a fixation rod or bone screw becoming inadvertently dislodged during installation. It will be noted that the plane of the O-rings 20 securing the part-balls on the brackets is similarly inclined.

In the embodiment illustrated, the locking screw 10 comprises a bolt extending through openings in the brackets 6,8 to a nut 32 mounted on the opposite side. The bolt has a head formed in two parts 34 and 36. Either part can be manipulated by hand during initial installation of the device, but when the device is to be secured only the part 36 is turned. Part 36 is a torque limiting element, and attached to the part 34 in such a manner that the attachment breaks once the torque applied exceeds a pre-set limit. This ensures that when the device is installed, the part-balls engage the fixation rod and bone screw with the right pressure. It will be noted in this respect that neither the brackets nor the ball parts should themselves be in engagement. They will be held apart by the fixation rod and bone screw.

Once the device is installed and in place, the O-rings 20 and 30 can be left in place or removed, as most appropriate to the particular circumstance.

The recesses in the brackets 6 and 8 in which the ball parts are received are defined by relatively narrow arcuate channels within the outline of each bracket. This allows for the creation of lateral recesses 38 on either side of the assembled device permitting a wide range of orientations for the fixation rod and bone screw. This versatility is illustrated in FIG. 3 which shows two bone screws 2 in each of two parts of a fractured bone, interconnected by three fixation rods 4. Multiple devices are used, and the bone screws are installed at different angles, to ensure that the fixation accomplished by the rods 4 holds the fractured bone parts in their proper orientation.

Figure 4:
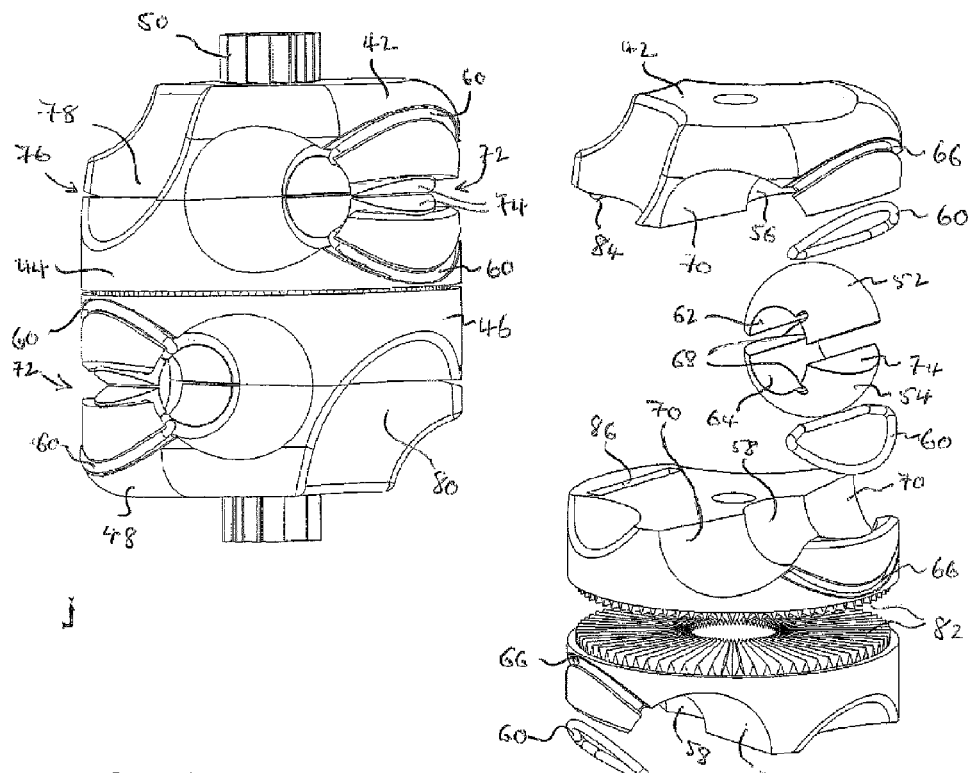
FIG. 4 is a side view of a device according to a second embodiment of the invention.
Figure 5:
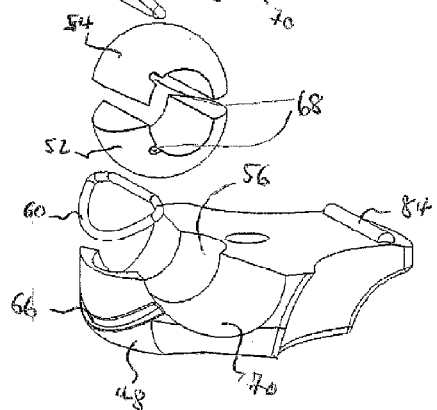
FIG. 5 is an exploded view of the device of FIG. 4.

The embodiment of FIGS. 4 and 5 has four brackets 42,44,46 and 48 held together by a locking screw 50. The brackets 42 and 44 form a first pair in which are mounted two part-balls 52 and 54. They are held in respective recesses 56 and 58 by elastic O-rings 60. Each part-ball has an exposed surface relative to the bracket in which it is mounted, and in that surface is formed a groove 62 which, when the ball parts unscrew are set in juxtaposition combines with the groove 64 in the opposing part-ball to form a sleeve for receiving a fixation rod or bone screw. As can be seen, the O-rings 60 are located in channels 66 and 68 formed respectively in the brackets and ball parts. In this way the part-balls are located relative to the brackets without interrupting the surface of the sleeve formed by the juxtaposed part-balls. The elasticity of the O-rings holding the part-balls in place, at least initially and until the rods or screws are installed, enables the part-balls to rotate in their recesses until the final orientation of the rods or screws is set, and the locking means tightened. However, it will be appreciated that all is required is that the part-balls are retained until they are held in place by the rods or screws. As an alternative to O-rings therefore, in all embodiments of the invention, a light adhesive can be used, or a linear coupling which may or may not be elastic, within each recess behind the respective part-ball. The curvature within the recess does not of course have to match that of the part-ball, and can be greater to create the required space. As with the O-rings, an adhesive or linear coupling can be biodegradable if desired, but it may be preferable to preserve the mounting or coupling to reduce the chance of a ball part being lost when the device is removed.

As in the embodiment of FIGS. 1 and 2, the arcuate channels 56 and 58 are relatively narrow, allowing for the creation of lateral recesses 70 with divergent walls; typically frustoconical, to provide for multidimensional orientation of a rod or screw held between the ball parts. Proper alignment of the brackets 42 and 44 is further assured by the engagement of ridge 84 on the bracket 42 in slot 86 in the bracket 44.

The construction and assembly of the brackets 46 and 48 and the respective ball parts and O-rings is essentially identical to that just described and corresponding parts are similarly identified. It will though, be noted that the juxtaposed faces of the brackets 44 and 46 are formed with radial grooves 82 which allow for the two pairs of brackets to be fixed at selected angular orientations. Thus, when the device is loosely assembled with the locking screw in place and fixation rods and/or bone screws installed, the two bracket pairs can be rotated one relative to the other before the final alignment of the rods and/or screws is set. Once it is, the locking screw or locking mechanism is tightened to secure the entire assembly.

In the embodiment of FIGS. 4 and 5, each ball part is substantially hemispherical in outline and, when in juxtaposition with its associated ball part, defines a plane that is substantially aligned with that of the juxtaposed brackets. As better shown in FIG. 4, each pair of ball parts is on one side of the locking screw 50, and the bracket surfaces in which the recesses or arcuate channels are formed are separated on the outer side of the channels to form an opening for receipt of a fixation rod or bone screw. The juxtaposed faces of the ball parts are also formed with chamfered surfaces 74. On the opposite side 76 of the bracket pair the bracket surfaces form a recess to create a pivot axis which further facilitates insulation of a fixation rod or bone screw. With the locking screw only loosely engaged, the opening 72 is enlarged by pivoting the brackets (42 and 44) about the pivot axis and this does of course also separate the ball parts to allow a fixation rod or bone screw to be installed in the sleeve formed thereby.

In the embodiment of FIGS. 4 and 5 the combination of brackets when assembled, have additional recesses 78 and 80. These facilitate the manual installation and orientation of the device up to and including the tightening of the locking screw with the fixation rods and/or bone screws in place.

The two embodiments of the invention particularly described operate in essentially the same way, and it will be appreciated that the embodiments of FIGS. 4 and 5 can be used in the same way as the embodiment of FIGS. 1 and 2 in the framework shown in FIG. 3. It will also be clear that many features of the two embodiments may be interchanged. Particularly, the misalignment of the plane of juxtaposition of the ball parts described with reference to FIG. 2 can be adopted in the embodiment of FIGS. 4 and 5 as can the chamfered surfaces 74 in the embodiment of FIGS. 4 and 5 be adopted in the embodiment of FIG. 2.

Devices of the invention can be used with a range fixation rods and bone screws of different diameter. It is not essential, although preferred, that their surface curvatures exactly match those of the grooves in the ball parts which form the sleeve in which they are received. However if required, the ball parts of a device can easily be removed and replaced by others with grooves better or precisely matching particular rods or screws. It will be appreciated in this respect that the juxtaposed faces of the ball parts will not normally engage with each other when a rod or screw is installed between them, but be spaced apart, as will be the brackets in which they are mounted, by virtue of the rods or screws.

The invention claimed is:

1. A bone fixation device for mounting a fixation rod on a bone screw, comprising a plurality of brackets, each defining a surface formed with at least one recess; part of a ball mounted in each recess with an exposed face formed with a groove for receiving a rod or screw, the brackets being held such that at least one pair of exposed ball faces are in juxtaposition to define a sleeve for said rod or screw; and means for urging the brackets and the exposed bail faces towards each other to clamp said rod or screw between at least one pair of juxtaposed ball faces, wherein each ball part is held in its respective recess by a resilient ball tie.

2. A device according to claim 1 wherein an even number of brackets are arranged in at least one pair, each bracket defining a surface with a single recess for a ball part mounted therein.

3. A device according to claim 1 wherein an even number of brackets are arranged in pairs, each bracket defining a surface formed with at least two recesses for ball parts mounted therein.

4. A device according to claim 1 wherein not all the brackets define surfaces formed with the same number of recesses; and wherein the brackets are arranged with one bracket defining a surface formed with a plurality of recesses whereby the exposed faces of ball parts therein can be in juxtaposition with the exposed faces of ball parts mounted in the surfaces of at least two other brackets.

5. A device according to claim 1 wherein the urging means acts along an axis and the juxtaposed ball faces are in planes other than perpendicular to said axis.

6. A device according to claim 5 wherein said bracket surfaces are planar and parallel, and wherein a plane defining the juxtaposition of a pair of ball faces traverses the plane of the respective bracket surfaces when a fixation rod is clamped between the ball faces.

7. A device according to claim 1 wherein the outline of each ball part is substantially a hemisphere.

8. A device according to claim 1 wherein the outline of each ball part is non-hemispherical, and complementary to its pair.

9. A device according to claim 1 wherein the ball tie is an elastic O-ring.

10. A device according to claim 1 wherein brackets are provisionally held against each other by a resilient bracket tie.

11. A device according to claim 10 wherein the bracket tie comprises elastic O-rings.

12. A device according to claim 1 wherein the ties are self-degrading in water.

13. A device according to claim 1 wherein the urging means comprises a locking screw for coupling associated brackets.

14. A device according to claim 13 wherein the locking screw extends through an opening in one of the brackets for engagement in a threaded section in another bracket.

15. A device according to claim 13 wherein the locking screw extends through openings in associated brackets for engagement with a threaded lock nut.

16. A device according to claim 13 wherein the locking screw comprises male and female threaded parts extending respective in aligned openings in associated brackets for engagement between distal ends of said aligned openings.

17. A device according to claim 13 wherein the locking screw has a torque-limiting element for tightening, wherein the element breaks off when the torque applied thereto exceeds a pre-set limit.

18. A device according to claim 1 wherein the recesses for the ball parts are defined by arcuate channels within the outline of each respective bracket.

19. A device according to claim 1 wherein associated brackets define lateral recesses on either side of the device for multidimensional orientation of said rod or screw held therein.

20. A device according to claim 1 wherein the brackets, the ball parts, and the urging means are made of carbon fibre.

* * * * *